(12) United States Patent
Murto et al.

(10) Patent No.: US 6,689,615 B1
(45) Date of Patent: Feb. 10, 2004

(54) METHODS AND DEVICES FOR PROCESSING BLOOD SAMPLES

(76) Inventors: James Murto, 10633-102$^{nd}$ Pl., Maple Grove, MN (US) 55369; Michael Salvati, 1424 Avon St., St. Paul, MN (US) 55117

( * ) Notice: Subject to any disclaimer, the term of this patent is extended or adjusted under 35 U.S.C. 154(b) by 174 days.

(21) Appl. No.: 09/679,130

(22) Filed: Oct. 4, 2000

(51) Int. Cl.$^7$ .................. G01N 33/86; G01N 33/53; B03C 1/30; C02F 1/48; B01J 19/12
(52) U.S. Cl. .................. 436/69; 436/16; 436/63; 436/71; 436/177; 436/178; 436/510; 436/524; 436/525; 436/526; 436/538; 436/539; 436/541; 436/806; 436/815; 436/817; 436/818; 436/824; 436/827; 210/222; 210/634; 210/644; 210/645; 210/695; 422/186.01
(58) Field of Search .................. 436/69, 510, 538, 436/539, 541, 16, 63, 71, 177, 806, 178, 524, 525, 526, 815, 817, 818, 824, 827; 210/634, 644, 645, 695, 222; 422/186.01

(56) References Cited

U.S. PATENT DOCUMENTS

| | | |
|---|---|---|
| 4,812,401 A | 3/1989 | Tarnowski et al. |
| 5,136,095 A | 8/1992 | Tarnowski et al. |
| 5,370,993 A | 12/1994 | Tarnowski et al. |
| 5,405,743 A | 4/1995 | Tarnowski et al. |
| 5,460,974 A * | 10/1995 | Kozak et al. .................. 436/71 |
| 5,536,644 A * | 7/1996 | Ullman et al. .............. 435/7.25 |
| 5,558,834 A * | 9/1996 | Chu et al. ...................... 422/55 |
| 5,622,831 A | 4/1997 | Liberti et al. |
| 5,639,669 A * | 6/1997 | Ledley ........................ 436/177 |
| 5,641,622 A * | 6/1997 | Lake et al. ..................... 435/2 |
| 5,652,148 A | 7/1997 | Doshi et al. |
| 5,660,798 A | 8/1997 | Doshi et al. |
| 5,662,824 A * | 9/1997 | Sang et al. .............. 252/62.56 |
| 5,725,774 A | 3/1998 | Neyer |
| 5,762,871 A | 6/1998 | Neyer |
| 5,766,552 A | 6/1998 | Doshi et al. |
| 5,821,073 A * | 10/1998 | Lee ............................ 435/7.92 |
| 5,830,766 A | 11/1998 | Attridge et al. |
| 5,856,203 A | 1/1999 | Robinson et al. |
| 5,858,238 A | 1/1999 | McRea et al. |
| 5,866,122 A | 2/1999 | Turecek et al. |
| 5,917,030 A | 6/1999 | Newman |
| 5,919,642 A | 7/1999 | Khanna et al. |
| 5,922,551 A | 7/1999 | Durbin et al. |
| 5,932,097 A * | 8/1999 | Wilson ........................ 210/222 |

(List continued on next page.)

FOREIGN PATENT DOCUMENTS

| | | | |
|---|---|---|---|
| WO | WO 99/26067 | 5/1999 | |
| WO | WO 02/26292 | * | 4/2002 |

OTHER PUBLICATIONS

Haik et al., "The Use of Biotinylated Lectin for Separating Red Cells from Whole Blood," *Biomolecular Engineering*, 2000, vol. 16, No. 5, First International Conference, Alberta Canada, Jun. 18–21, 1 pg.

Higgins and Ko, "Duck lymphocytes. VII. Selection of subpopulations using lectin–coated magnetic beads," *Veterinary Immunology and Immunopathology*, 1995, 44:181–195.

*Primary Examiner*—Jill Warden
*Assistant Examiner*—Monique T. Cole
(74) *Attorney, Agent, or Firm*—Fish & Richardson P.C.P.A.

(57) ABSTRACT

Approaches are described for separating plasma from whole blood samples and include the use of magnetically attractable particles associated with an agglutinating agent. The magnetically attractable particles bind the cellular components in a whole blood sample. Application of a magnetic field gradient to a container with the blood sample and the magnetically attractable particles draws the particles to the surface of the container near the source of the magnetic field gradient. The plasma can be removed and stored or used for monitoring or detecting analytes in the plasma.

53 Claims, 3 Drawing Sheets

U.S. PATENT DOCUMENTS

| | | | |
|---|---|---|---|
| 5,939,331 A | | 8/1999 | Burd et al. |
| 5,980,479 A | * | 11/1999 | Kutushov .................. 604/5.04 |
| 6,033,574 A | * | 3/2000 | Siddiqi ....................... 210/695 |
| 6,036,857 A | | 3/2000 | Chen et al. |
| 6,106,732 A | * | 8/2000 | Johnston et al. ............ 210/767 |
| 6,132,607 A | * | 10/2000 | Chen et al. .................. 210/208 |
| 6,136,549 A | * | 10/2000 | Feistel ......................... 435/7.1 |
| 6,153,113 A | * | 11/2000 | Goodrich et al. ........... 210/782 |
| 6,291,249 B1 | * | 9/2001 | Mahant et al. .............. 436/177 |
| 6,365,417 B1 | * | 4/2002 | Fleming et al. ............. 436/514 |

* cited by examiner

METHODS AND DEVICES FOR PROCESSING BLOOD SAMPLES

BACKGROUND OF THE INVENTION

This invention relates to processing of blood samples. In particular, this invention relates to processing of whole blood samples to separate the cellular components in the blood samples from the liquid fractions.

Blood sample analyses are routinely performed to address a number of health concerns. Detection and/or quantitation of physiological compounds, for example, cholesterol, hormones, metabolites and the like can provide valuable information regarding the health of an individual. Generally, a blood sample is obtained from the patient at a health care facility such as a hospital, an emergency room and/or a physician's office and sent to a clinical laboratory for further processing.

In order to analyze the blood sample for the desired compounds and/or analytes, the cellular components from the whole blood samples are generally separated from the plasma, i.e. the liquid fraction of the blood. The cellular components of blood include, for example, erythrocytes, leukocytes and platelets. The erythrocytes are the most abundant. Erythrocytes can also interfere with assays due to their chromogenic nature.

Centrifugation is most commonly performed as the first step in a blood sample analysis to separate the cellular, i.e. semi-solid components, from the liquid component of the blood. The centrifugation is generally performed in a clinical laboratory after the blood sample is transported from the blood sample acquisition site. After centrifugation, the liquid component, i.e. the plasma is generally used for the desired analysis. The analysis of plasma for the desired analytes is conducted in automated or semi-automated systems, for example, diagnostic analyzers.

The steps of acquiring the blood sample, sending it to a clinical laboratory and centrifuging the blood samples prior to the desired analysis has considerable setbacks. First, the process is labor intensive and time consuming. Second, these procedures can expose laboratory staff to hazards of infection from handling patients' samples. In fact, several studies have shown that the lifetime risk of hepatitis B virus infection among health-care workers who have frequent contact with blood is between 15 and 30 percent or about 50–100 times the risk in the general population. (J. L. Dienstag, et al., Amer. J. Epidemiol., vol.115, pages 26–39, 1982 and B. S. Levy, et al., Amer. J. Epidemiol., vol. 106, pages 330–335, 1977) Transcription errors, specimen mix-ups and other mishandling are also common problems.

More recently, integrated blood-collection and processing systems have been introduced to serve the fully automated labs. A significant engineering effort has been invested in the development of sophisticated robust centrifuges that are needed to separate the blood cells in these large volume samples. The entire blood-processing and presentation process is highly labor-intensive and consumes more than 30 minutes. Thus, there is a great need for methodologies, protocols and equipment to effectively automate the blood sample preparation process in semi- and fully automated labs that are serving a wide variety of diagnostic instruments.

Sample centrifugation, usually at greater than 2000 revolutions per minute (rpm) for up to 10 minutes, is a step that affects the time to result. The analytical throughput of clinical analyzers can be limited by a lengthy preanalytical phase during which samples are prepared for analysis. Present sample processing procedures are limiting factors in fully realizing the high efficiencies potentially available with existing analytical instrumentation and are also slowing the delivery of test results at patient bed site, emergency room, and the like. These time consuming processes are also preventing the full implementation of physician-office diagnostics.

There is an increasing need for the ability to separate whole blood cellular components from the plasma of the blood sample at the blood sample acquisition site, i.e. in a physician's office, an emergency room or a patient's home. The plasma can then be used immediately, if desired, in a diagnostic test by the patient and/or the health care worker at the sample acquisition site, thus eliminating or reducing the use of clinical laboratory personnel for performing diagnostic tests.

A significant emphasis is currently being placed in the health care field related to the ability to provide desired results faster and in a more cost-efficient manner. Thus, procedures that eliminate or reduce the time required to conduct some of the labor-intensive steps can improve the time to result and reduce the costs.

SUMMARY OF THE INVENTION

In a first aspect, the invention pertains to a method for processing a blood sample to separate whole blood cellular components from plasma. The method includes contacting the blood sample with magnetically attractable particles associated with an agglutinating agent selected to bind to the whole blood cellular components in the blood sample. The method also includes subjecting the blood sample with the magnetically attractable particles to a magnetic field gradient to separate the magnetically attractable particles from the plasma.

In a further aspect, the invention pertains to a method for assaying a blood sample for the presence of one or more analytes. The method includes assaying an aliquot of plasma for the analyte or analytes. The method for obtaining the plasma includes processing the blood sample to separate the whole blood cellular components from plasma by contacting the blood sample with magnetically attractable particles associated with an agglutinating agent. The agglutinating agent is selected to bind to the whole blood cellular components in the blood sample but not the analyte or analytes being assayed. The method also includes subjecting the blood sample with the magnetically attractable particles to a magnetic field gradient to separate the magnetically attractable particles from the plasma.

In yet another aspect, the invention pertains to a device for processing a blood sample to separate the whole blood cellular components from plasma. The device includes a container having magnetically attractable particles associated with an agglutinating agent. The volume of the magnetically attractable particles in the container is selected such that when a magnetic field gradient is applied to a suspension of the particles, the particles accumulate in less than about 5 minutes at a surface of the container closest to the magnetic field gradient.

In a further aspect, the invention pertains to a reagent to separate whole blood cellular components from plasma in a blood sample. The reagent includes magnetically attractable particles associated with an agglutinating agent. The volume of magnetically attractable particles is selected to process a blood sample such that when the particles are in suspension, the particles are drawn away from the liquid of the blood sample in less than about five minutes when a magnetic field gradient is applied.

DETAILED DESCRIPTION OF THE PREFERRED EMBODIMENTS

Figure 1A:
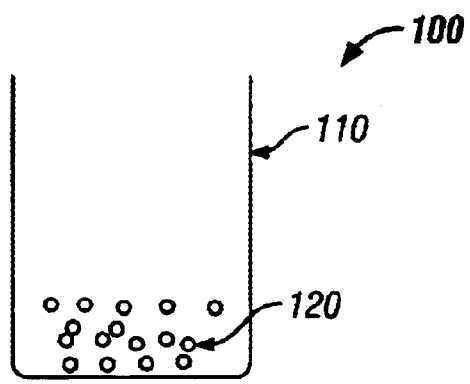
FIG. 1a is an illustration of a blood processing device.

Novel approaches are described for the separation of plasma from cellular blood components of whole blood samples. These approaches include the use of magnetically attractable particles associated with agglutinating agents. The agglutinating agents can efficiently bind the cellular components, particularly the red blood cells, in the blood sample. Application of a magnetic field gradient to a container including the blood sample can draw the magnetically attractable particles, having bound cellular components, to the surface of the container closest to the source of the magnetic field gradient. The liquid fraction of the blood sample, i.e. the plasma, can be separated from the magnetically attractable particles and used for further analysis or storage.

Composite separation particles include magnetically attractable particles associated with an agglutinating agent that can bind cellular components of a whole blood sample. The magnetically attractable particles can be advantageously efficient in binding the cellular components in blood samples and yielding plasma when exposed to a magnetic field gradient. Generally, at least about 0.02 micrograms of agglutinating agent can be associated with about 1 milligram of the magnetically attractable particles. Preferably, at least about 0.2 micrograms, and more preferably about 2 micrograms, of agglutinating agent is associated with about 1 milligram of the magnetically attractable particles.

The processing time for obtaining plasma from a blood sample can be less than about 5 minutes and in some embodiments, less than about 3 minutes when exposed to a magnetic field gradient. Generally, at least about 90 percent of the red blood cells, preferably greater than about 95 percent of the red blood cells and more preferably greater than about 99 percent of the red blood cells in a blood sample can be bound by the magnetically attractable particles.

A reagent for processing blood samples can include the magnetically attractable particles. The reagent can be used for obtaining plasma from a blood sample. Agglutinating agents associated with the magnetically attractable particles can bind cellular components of a blood sample when suspended in the blood sample. In particular, the reagents preferably are used for obtaining plasma from a blood sample in a short time, preferably in less than about 5 minutes. Plasma can be obtained by exposing the magnetically attractable particles suspended in the blood sample to a magnetic field gradient to draw the particles, with bound cellular components, toward the source of the magnetic field gradient. The reagent can be used in combination with other reagents to perform blood sample analyses.

In one embodiment, a device for processing blood samples includes a container having the magnetically attractable particles associated with an agglutinating agent. The magnetically attractable particles in the container can be contacted with a blood sample. The device may include an article that can generate a magnetic field such as a magnet. Application of a magnetic field gradient to the container can separate the magnetically attractable particles with the bound cellular components from the liquid fraction of the blood. Following removal of cellular components, the liquid fraction can be used for further analysis.

Methods for processing whole blood samples include using magnetically attractable particles associated with agglutinating agents. The blood samples can be contacted with the magnetically attractable particles, preferably, by suspension in the blood sample. The agglutinating agents can bind the cellular components of the blood samples. A magnetic field gradient can be applied to the magnetically attractable particles in order to draw the magnetically attractable particles that have bound cellular components toward the source of the magnetic field gradient. The particles accumulate, generally near the surface(s) closest to the magnetic field gradient source, resulting in a liquid fraction substantially free of the particles. The supernatant or liquid fraction of the sample can be removed and used for further analysis. The liquid fraction derived from a blood sample after processing with the magnetically attractable particles, as described herein, is referred to as plasma. Plasma as used herein includes all liquid blood fractions derived from whole blood including, for example, serum. Separation of the plasma from the cellular components can be accomplished expeditiously using the methods described herein. The processing time using the methods described herein, i.e. time from contact of the blood sample with the magnetically attractable particles to separation of plasma from the particles with bound cellular components can be short. These methods are particularly amenable to automation.

Analysis of blood samples for analytes can also be performed using the methods of the present invention. Blood samples can be collected and treated with magnetically attractable particles associated with the agglutinating agents. The agglutinating agent can be selected to bind cellular components of the sample but not the analyte to be assayed.

Magnetically attractable particles can be contacted with the blood sample and separated from the plasma after or during binding of the cellular components of the whole blood sample by using a magnetic field gradient. All of the plasma or an aliquot of the plasma can be used to analyze the presence and/or the concentrations of one or more analytes in a variety of assays. The blood processing procedures using the magnetically attractable particles, as described herein, can be adapted for use in conjunction with assays performed in automated or manual diagnostic analyzers, for example, fully automated systems, semiautomated systems, lateral flow devices and the like.

The use of the magnetically attractable particles of the present invention, preferably in conjunction with a magnetic field gradient, can advantageously streamline the overall diagnostic processes involving blood analysis and reduce the health risk associated with handling patients' samples. In particular, the time to obtain a clinically relevant answer regarding a patient's health is reduced. In some embodiments, plasma can be obtained from whole blood samples in less than about five minutes. Furthermore, with small sample volumes, plasma may be obtained in about three minutes or less. Time to result, thus, can be significantly improved in a number of settings including emergency rooms and physicians' offices. High throughput analyzers used in hospital laboratories and reference laboratories can also be used in point of care environments when methods described herein are used for processing blood samples since the overall time from specimen collection to test results printout is significantly reduced.

A number of methods have been described in the literature for processing blood samples without centrifugation. These include methods described in, for example, U.S. Pat. Nos. 5,660,798 and 5,652,148 both issued to Doshi et al. These methods include agglutinating the red blood cells and filtering the blood samples to obtain the plasma. These procedures, however, can involve significant handling of samples by personnel and are generally not adaptable to automated systems.

A. Blood Samples

The magnetically attractable particles of the present invention can be used to process whole blood samples. Whole blood includes a liquid fraction and cellular components. Plasma is a liquid fraction of the blood. The cellular components include the blood cells and platelets suspended in the liquid. Blood cells include red blood cells (RBC), i.e. erythrocytes, and white blood cells (WBC), i.e. leukocytes. "Cellular components" refers to whole cells in a whole blood sample including, for example, RBC, WBC and platelets.

In whole blood samples, the cellular components are suspended in the liquid fraction. The liquid fraction accounts for about 55 percent by volume of the total volume of the blood and is referred to as plasma. Plasma includes about 92 percent by weight water, about 7 percent by weight protein and about 1 percent by weight of other substances. Proteins found in plasma include globulins, albumin and fibrinogen. Plasma from which fibrinogen has been removed is called serum.

Whole blood samples that can be processed in the present invention include blood collected from a variety of sources. The blood samples can be from animals, especially mammals. Preferably, the blood samples are from humans.

The blood samples can be collected by the patient, a health care worker, for example, a nurse, or a medical technician. The blood samples can be collected by a finger prick, by drawing from a vein and the like.

The volume of blood sample that can be processed can vary. Suitable volumes of blood samples are preferably between about 10 microliters and 10 milliliters. More preferably, the volume of the blood sample is between about 20 microliters and 10 milliliters.

The blood sample is generally collected in a collection device, for example, a vial, a tube and the like. Preferably, the blood sample is collected in a collection device having a sealable opening. The blood sample may be processed in the collection device in which the blood sample was collected. In other words, the magnetically attractable particles may be added to the container in which the sample was collected. Alternatively, the blood sample may be transferred to another container having the magnetically attractable particles. In yet another embodiment of the invention, the blood sample may be collected in a container already having the magnetically attractable particles coated with the agglutinating agent.

The blood sample may be collected in a collection device that optionally, includes anti-coagulants, non-hemolytic surfactants and/or agglutinating agent coated magnetically attractable particles. Preferably, the collection device, with or without the particles, includes anti-coagulants and more preferably anti-coagulants and non-hemolytic surfactants. Generally, the blood is processed immediately or shortly after collection.

Anti-coagulants can include, for example, EDTA, heparin, citrate and the like. Blood samples exposed to anti-coagulants can result in reducing clumping or aggregation of cellular material. Thus, exposure of blood samples to magnetically attractable particles associated with both agglutinating agents and to anti-coagulants can enhance the separation of the cellular components and the plasma.

Non-hemolytic surfactants may also be included in the collection device. The surfactants may be anionic, cationic or nonionic surfactants. A preferred surfactant is a non-ionic, non-hemolytic surfactant. Suitable non-hemolytic surfactants include, for example, TWEEN 20 (polysorbate 20), a sorbitan monolaurate including about twenty moles of ethylene oxide; the SILWET surfactant (dimethicone polyols), the ethylene oxide or propylene oxide modified polymethylsiloxanes available from Union Carbide Corp., Danbury, Conn.; PLURONIC L-GH (poloxamer 184), a propylene oxide/ethylene oxide copolymer available from BASF Corp. Wyandote, Mich.; and TRITON X-405 (Octoxynol 40) octyphenol ethoxylated with about 40 moles of ethylene oxide and TRITON X-45 (octoxynol 5), octyphenol ethoxylated with about 5 moles of ethylene oxide, available from Rohm and Nass Company, Philadelphia, Pa.

B. Magnetically Attractable Particles

Magnetically attractable particles associated with an agglutinating agent can be used to bind the cellular components of a whole blood sample. In preferred embodiments, the volume of magnetically attractable particles used can bind a high percentage of the cellular components, particularly the red blood cells, in a whole blood sample. Separation of the magnetically attractable particles from the liquid fraction can provide plasma that can be stored or used for further analysis.

Magnetically attractable particles for binding the cellular components generally include particles that are intrinsically magnetically attractable or have been rendered magnetically attractable by, for example, attachment to a magnetically responsive substance or by incorporation of such substance into the particles. The magnetically attractable particles can be paramagnetic or ferromagnetic. Preferably, the magnetically attractable particles are paramagnetic. Paramagnetic materials, when placed in a magnetic field gradient, are magnetized parallel to the field. In other words, paramagnetic materials have the property that they are only magnetic when placed in a magnetic field gradient. Once the field is removed, the particles with the paramagnetic material can cease to be substantially magnetic and can generally easily be dispersed into suspension.

The magnetically attractable particles generally are insoluble in water and/or plasma such that the particles maintain the particulate nature. Suitable magnetically attractable particles can include a variety of materials including for example, complex salts and oxides, borides, and sulfides of iron, cobalt, nickel and rare earth elements having high magnetic susceptibility. The magnetically attractable particles can include iron oxide particles, chromium oxide particles and the like. The magnetically attractable particles can also include magnetite, hematite, ferrite and the like. In one preferred embodiment, the magnetically attractable particles include pure iron oxide particles. In another preferred embodiment, the magnetically attractable particles include iron oxide particles such as magnetite.

Magnetically attractable particles can be particles that include a proportion of magnetite. Preferably, the magnetically attractable particles are encapsulated magnetite particles. The amount of magnetite in magnetically attractable particles can be between about 20 percent by weight of magnetite and about 60 percent by weight of magnetite. Preferably, the magnetically attractable particles are between about 25 and about 35 percent by weight magnetite.

The magnetically attractable particles may be coated with a polymer prior to association with the agglutinating agent to reduce nonspecific binding of proteins in the blood sample (such as the analyte being measured or detected) on the surface of the particles. Such polymers may be coated on the surface of the magnetically attractable particles using any known methods such as silanization, encapsulation and the like. The iron oxide particles may be treated, for example, silanized prior to association with an agglutinating agent. The magnetically attractable particles can be silanized by treating the particles with silane. Silanization is known in the art and can include immersing the particles in a silane solution. The magnetic material of the magnetically attractable particles can be encapsulated by any number of materials, preferably polymeric materials. The magnetic material can be encapsulated by, for example, latex, cellulose, polyacrolein, polyacrylamide, silane and the like.

The size and type of the magnetically attractable particles can vary and is generally selected such that a volume of the magnetically attractable particles can be drawn or pulled out of suspension within a short time. The magnetically attractable particles are selected such that they can be pulled out of suspension by a selected magnet or magnets in less than about 5 minutes and preferably in less than about three minutes.

Generally, the diameter of the magnetically attractable particles can be between about 0.025 microns and about 200 microns. Preferably, the diameter of the magnetically attractable particles is between about 0.1 microns and about 100 microns, more preferably between about 0.1 microns and about 10 microns. The mean diameter of the magnetically attractable particles preferably is between about 0.2 microns and about 2 microns, and more preferably between about 0.8 microns and about 1.2 microns.

The magnetically attractable particles described herein can be associated with agglutinating agents. Agglutination includes clumping of cells and/or precipitation of complex carbohydrates. Suitable agglutinating agents include, for example, lectins. Preferably, the lectins are not specific to a particular blood group or type. Lectins are proteins, widely found in nature, that are able to agglutinate RBC and other types of cells. Lectins occur primarily in plant seeds but they also occur, for example, in roots, leaves, bark, fungi, bacteria, seaweed, sponges and fish eggs. In addition, lectins can be found in invertebrates such as clams, snails and horseshoe crabs. Suitable lectins include, for example, *Abrus precatorius* (abrin, Jequirty bean), *Agaricus bisporus* (mushroom), *Bauhinia purpurea* (camels foot tree), *Caragana arborescens* (Siberian pea tree), *Cicer arietinum* (chick pea), *Codium fragile* (Green marine algae), *Canavalia ensiformis* (ConA, Concanavalin A, Jack Bean) *Datura stramonium* (jimson Weed), *Glycine max* (soybean), *Lathyrus odoratus* (Sweet Pea), *Lens sulinans* (Lentil), *Limulus polyphemus* (Horseshoe crab, Limulin), *Lycopersicon esculentum* (Tomato), *Maclura pomifera* (Osage orange), *Mycoplasma gallisepticum, Naja mocambique* (cobra venom), *Naja naja kaouthia* (cobra venom), *Perseau americana* (Avocado), *Phaseolus coccineus* (Scarlet runner bean), *Phaseolus vulgaris* (Red Kidney bean), *Phytolacca americana* (Pokeweed), *Pisum sativum* (garden pea), *Pseudomonas aeruginosa, Psophacarpus tetragonolobus* (winged bean), *Ricinus communis* (Castor bean), *Robinia pseudoacacia* (black locust, false acacia), *Sambucus nigra* (elder), *Solanum tuberosum* (potato), *Triticum vulgaris* (Wheat germ), *Vicia faba* (fava bean, broad bean), *Vicia Sativa, Vigna radiata* (Mung bean), *Viscum Album* (European mistletoe), *Wisteria floribunda* (Japanese wisteria) and the like.

Lectins have been known and are discussed, for example, in Schnebli, H. P. et al. "Reaction of Lectins with Human Erythrocytes" Expt. Cell Research, 91, (1975) incorporated herein by reference. Lectins can often be blood group specific and have been used in blood grouping, polyagglutination studies and various histochemical studies of normal and pathological conditions. Preferably, the lectin associated with the magnetically attractable particles binds non-specifically to the cellular components of a variety of blood samples. An agglutinating agent that has a broad specificity, thus, is preferable. In preferred embodiments, the agglutinating agent is Solanum Tubersum Agglutinin (STA) that can be purchased from, for example, Sigma Chemical Co. St. Louis, Mo.

The agglutinating agent can be associated with the magnetically attractable particles using a variety of suitable methods. As referred to herein "associated with" with respect to the magnetically attractable particles means that a stable interaction between the particles and the agglutinating agent was formed and maintained by covalent or noncovalent means. In the context of this invention, the terms "bound to", or "immobilized" or "coated to" encompasses all mechanisms for binding agglutinating agents, such as lectins, to magnetically attractable particles. Such mechanisms include, for example, covalent bonding, non-covalent binding, chemical coupling, absorption by hydrophobic/hydrophobic, hydrophilic/hydrophilic, or ionic interactions and the like. Preferably, the magnetically attractable particles are coated with the agglutinating agent. Passive adsorption of the agglutinating agent is described, for example, below in Examples 1 and 3. Passive adsorption can include non-specific association of the agglutinating agent with the surface of the magnetically attractable particles that is, generally, substantially irreversible. To obtain passive adsorption, the magnetically attractable particles can be incubated with the agglutinating agent in appropriate buffers for a suitable length of time. The buffer can be, for example, bicarbonate buffers, phosphate buffers and the like. The magnetically attractable particles and the agglutinating agent can be incubated together, for example, for several hours or overnight to adsorb the agglutinating agent to the magnetically attractable particles. Other buffers and incubation times can also be appropriate.

The agglutinating agent may be covalently coupled to the magnetically attractable particles in alternative preferred embodiments. The agglutinating agent may be covalently coupled to the magnetically attractable particles using the binding properties of known functional groups. An embodiment of covalent coupling of the agglutinating agent to the magnetically attractable particles is illustrated in example 2 below. For example, the covalent bonding can involve the reaction of the amino functional group of the agglutinating agent with the carboxyl group on the magnetically attractable particles and a carbodiimide reagent like 1-[3-

(dimethyl amino)propyl]-3-ethyl-carbodiimide (EDC) as the dehydration component. The covalent bonding may also include the use of linker molecules between the magnetically attractable particles and the agglutinating agent. The linker molecules can include difunctional groups, either equivalent or different, photoactivatable groups, and the like.

The magnetically attractable particles may also be associated with anti-coagulants and/or non-hemolytic surfactants in addition to the agglutinating agents. Anti-coagulants and non-hemolytic surfactahts generally work synergistically with the agglutinating agents to separate the cellular components from the plasma. Other compounds that enhance the separation of cellular components from the plasma may also be associated with the particles. Magnetically attractable particles may include both agglutinating agents and non-hemolytic surfactants. Alternatively, magnetically attractable particles may include simultaneously agglutinating agents, coagulants and non-hemolytic surfactants.

The amount of agglutinating agent that is associated with the magnetically attractable particles can vary depending on the diameter of the magnetically attractable particles and the particular agglutinating agent selected. Generally, the amount of agglutinating agent that can be associated with the particles increases as the diameter of the magnetically attractable particles increases. Desirable particles generally have higher amounts of agglutinating agents associated with the particles. Furthermore, as the amount of agglutinating agent on the magnetically attractable particles increases, the speed at which the plasma can be acquired also increases. Particles that are too large, however, may not provide desirable surface area for efficiently binding the cellular components in the sample.

Generally, the concentration of agglutinating agent is at least about 0.02 micrograms of agglutinating agent per milligram of magnetically attractable particles. Preferably, the concentration of agglutinating agent is between about 0.1 micrograms of agglutinating agent and about 10 micrograms of agglutinating agent per milligram of magnetically attractable particles. More preferably, the concentration of agglutinating agent is between at least about 1 microgram of agglutinating agent per milligram of magnetically attractable particles and about 5 micrograms of agglutinating agent per milligram of magnetically attractable particles. Even more preferably, the concentration of the agglutinating agent is about 2 micrograms of agglutinating agent per milligram of magnetically attractable particles.

The amount of agglutinating agent that is associated with the magnetically attractable particles can also be dependent on the specific lectin selected. Some lectins, for example, may have a higher affinity for the magnetically attractable particles than other lectins. Lectins with high affinity are generally desirable, however, in some embodiments, lectins with lower affinity may be desirable. In some embodiments, for example, the higher affinity lectins may also bind the analyte or analytes that is to be ultimately detected or monitored in the plasma. Lectins with a lower affinity may be selected because they do not bind the analyte to be detected or monitored in the plasma.

The magnetically attractable particles described herein can be advantageously efficient in binding the cellular components of a blood sample. Generally, the amount of magnetically attractable particles used for processing a blood sample can bind at least about 90 percent of the red blood cells in the blood sample. Preferably, the amount of the magnetically attractable particles can bind at least about 95 percent, and more preferably at least about 99 percent, of the red blood cells in the blood sample.

The concentration of the magnetically attractable particles in suspension is generally between about 0.1 percent by weight solids and about 20 percent by weight solids, preferably between about 0.5 percent by weight solids and about 15 percent by weight solids. Preferably, the concentration of the volume of the particle suspension is between about 1 percent by weight and about 10 percent by weight.

The magnetically attractable particles with the associated agglutinating agent can be used as a suspension. The magnetically attractable particles can be separated from the liquid as described below. The blood sample can then be added to the separated magnetically attractable particles to form a new suspension. The liquid suspension of the agglutinating agent coated magnetically attractable particles can include a variety of buffers including, for example, fish skin gelatin buffer, a glycine storage buffer and the like.

Alternatively, the agglutinating agent coated magnetically attractable particles may be used as dry reagents. The liquid from the volume of magnetically attractable particles suspension can be separated from the particles. The magnetically attractable particles can then be dried. Drying of the magnetically attractable particles can be performed in a variety of ways including, for example, air drying, lyophilization, oven drying, vacuum oven drying and the like. In some embodiments, the particles can be assembled into a tablet form. Tablets can be assembled by commercial vendors, for example, by Biolyph, Minnetonka, Minn.

The magnetically attractable particles described herein can be a used as a reagent for processing blood samples to separate the cellular components from the plasma. The amount of the magnetically attractable particles used can vary and be determined by, for example, the concentration of the agglutinating agent on the particles, the size of the blood sample to be evaluated and the speed at which the result is desired.

Generally, at least about 5 micrograms of the magnetically attractable particles can bind about 90 percent of the red blood cells in a 100 microliter of blood sample. Preferably, at least about 20 micrograms of the magnetically attractable particles are used to bind about 90 percent of the red blood cells in a 100 microliter of blood sample. More preferably, at least about 100 micrograms of the magnetically attractable particles are used to bind about 90 percent of the red blood cells in a 100 microliter of blood sample.

The amount of magnetically attractable particle reagent used can advantageously separate the cellular components from the plasma in a blood sample in less than about 5 minutes, preferably, in less than about 3 minutes and more preferably in less than about 2 minutes.

The reagent can be a liquid suspension of the particles. Alternatively, the reagent can include a dried form of the magnetically attractable particles.

C. Blood Sample Processing Device

One embodiment of a device of the present invention includes a container with magnetically attractable particles. The device may include an article for generating a magnetic field gradient. The device may also include a number of other components for processing plasma derived from a blood sample that is contacted with the magnetically attractable particles. In particular, the device can include components that provide automated processing of the blood sample.

The container can be, for example, a vial, a cup, a tube and the like. The container can be made from glass or polymers, for example, polypropylene. The container generally can receive at least about 50 microliters of blood sample. Preferably, the container can receive at least about 100 microliters of blood sample. In some embodiments, the containers may be large enough to receive between about 1 milliliter and about 10 milliliters of sample. The size of the container can depend on the specific environment where the separation will occur, i.e. automated system, at home use and the like. The size of the container may also depend on the size of the sample to be processed. In pediatric applications, for example, the sample size may be small and thus, the container may be small.

The blood sample can be collected directly in the container. Alternatively, the blood sample can be collected in a collection device and then transferred to the container. In some embodiments, all of the collected blood sample from the collection device can be added to the container. In other embodiments, an aliquot of the collected blood sample can be added to the container having the magnetically attractable particles. The container may, optionally, include anticoagulants and/or non-hemolytic surfactants. The size of the blood sample collected can be dependent on the ultimate use of the plasma.

The blood processing device may be manually operated by an individual. Alternatively, the blood processing device can be an automated or a semi-automated device. The plasma derived from blood processing using the magnetically attractable particles can then be used in diagnostic assays.

A manually operated blood processing device can include a container with the magnetically attractable particles. In use, a blood sample can be added to the container by a operator. After suspension, the operator can place the container in a magnetic field gradient to separate the plasma from the magnetically attractable particles. The magnet for generating the magnetic field gradient may, optionally, be part of the device. The separated plasma can be removed from the container by the operator using a variety of techniques described below. The plasma can then be used for a variety of analyses including analysis performed manually or in automated devices.

A suitable blood processing device can be an automated device or a semi-automated device. A blood sample, for example, can be placed in a cup of the automated device. An exemplary automated device may perform the following operations: remove an aliquot of the blood sample from the cup, combine and suspend the blood sample with the magnetically attractable particles in a container, and apply a magnetic field gradient to separate the plasma from the particles. In addition, the device may remove plasma from the container and place it in a different receptacle for further use or storage.

In some embodiments, the blood processing device can be adapted to be a part of a larger automated or semiautomated device that also analyzes the separated plasma for presence of one or more analytes. An example of an automated device is the Abbott $IM_x$ system available from Abbott Laboratories, Chicago, Ill. or a Copalis II system described in example 9. For example, the device can receive one or more vials of blood samples in a tray. The device may transfer the blood sample from the vials into containers with the magnetically attractable particles. If the tray has multiple samples, the samples may be processed sequentially or simultaneously. The blood samples can be processed to obtain plasma using the magnetically attractable particles. The magnet for separating the magnetically attractable particles may be incorporated into the device. The plasma can then be used to conduct further diagnostic assays for detecting or monitoring the analytes in the sample.

The plasma analysis components of devices can include a number of articles and reagents for carrying out the diagnostic assays. The plasma analysis components can include articles, for example, pipetting devices for removing the plasma, additional tubes or containers for conducting the assays, analytical components such as computers and the like. The plasma analysis components can also include reagents necessary for the assays, for example, binding partners of the analytes, indicators and the like. The specific components can vary and are dependent on the method used to conduct the assays and the specific assays to be performed.

Lateral flow devices can also be used in conjunction with the blood processing devices described herein. Lateral flow devices are described, for example, in U.S. Pat. No. 5,939,331 issued to Burd et al. which is incorporated herein. Lateral flow devices generally include a solid support with one or more zones and generally one or more reagents in the zones. Generally, the sample is placed at one end of the solid support. The sample travels through the various zones by capillary action. As the sample travels through the different zones, it can potentially react with the reagents present in each of the zones, preferably sequentially.

Figure 1B:
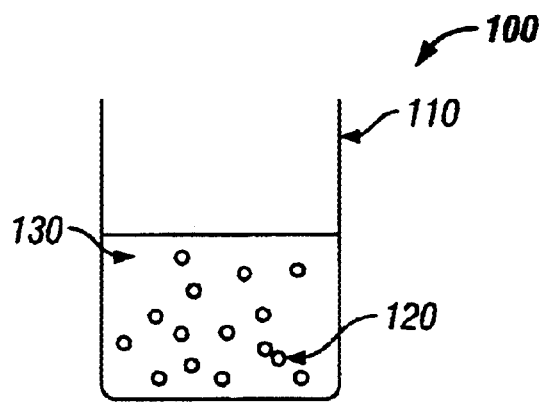
FIG. 1b is an illustration of the device of FIG. 1a with a blood sample.
Figure 1C:
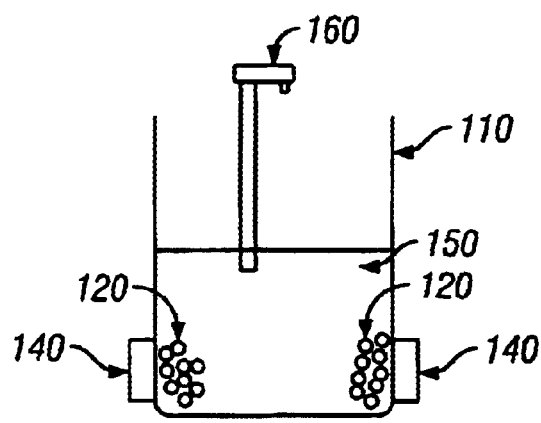
FIG. 1c is an illustration of the device of FIG. 1b with a magnet and a pipetting device.

FIG. 1a–FIG. 1c illustrate an example of a blood processing device and the use of the device. Device 100 shown in FIG. 1a includes container 110 and magnetically attractable particles 120. FIG. 1b includes addition of blood sample 130 and suspension of particles 120 in blood sample 130. FIG. 1c includes magnets 140 placed proximal to container 110 to separate the particles 120 with bound cellular components from plasma 150. A pipetting device 160 can be used to remove plasma 150 from container 110 and dispense it whenever required.

The container generally includes magnetically attractable particles having associated agglutinating agent. The magnetically attractable particles may be placed in the container prior to addition of the blood sample. Alternatively, the magnetically attractable particles may be placed in the container after addition of the blood sample into the container. The magnetically attractable particles, as described above, can be in the liquid form or the dry form. If the liquid form is used, the liquid preferably is separated from the particles prior to contacting the particles with the blood sample.

The magnetically attractable particles are generally suspended in the blood sample by, for example, mixing to enhance the efficiency of binding of the cellular components to the agglutinating agent on the particles. The container is generally subjected to a magnetic field gradient after the magnetically attractable particles have substantially bound the cellular components in the whole blood sample. Suitable magnets can vary in size, shape and magnetic strength and include, for example, a neodymium magnet.

The size of the magnet can depend on the specific location of the magnetically attractable particles. A small container with magnetically attractable particles to be used by an individual can have a small magnet. If large volumes of samples are to be processed, i.e. 10 milliliters, a larger and/or stronger magnet may be desirable.

The strength of the magnet can vary. Magnetic strength is expressed in units of gauss. The strength of the magnet can determine the efficiency of separation of the magnetically attractable particles from the plasma. Stronger magnets can advantageously reduce the separation time and thus, the processing time of the blood sample. The strength of the desired magnets can be between about several hundred gauss and about several kilo gauss. Preferably, the strength of the magnets is between about 1000 gauss and about 20,000 gauss. More preferably, the strength of the magnets is between about 10,000 gauss and about 14,000 gauss.

The magnet shape can be desirably selected. In some embodiments, the shape of the magnet can be adapted to the container in which the sample is to be placed. The magnet may be shaped, for example, to surround the outside portion of a container as illustrated in FIG. 1a or the bottom of a container. Preferably, the magnet is on a side surface of the container near the bottom so that a pipet can be inserted from the top to draw off the plasma without disturbing the particles. The shape of the magnet can be, for example, rectangular, disc-like, horseshoe shape and the like.

The magnet can be positioned at the surface of the container when the presence of a magnetic field gradient Is desirable for separation of the particles from the plasma. The magnetic field gradient can, preferably, also be removable when desired. In other words, it is desirable to have a magnetic field gradient that can be removed or switched off during some of the processing steps.

Generally, the magnetically attractable particles are suspended in the container in the blood sample. After appropriate suspension and binding of the cellular components by the magnetically attractable particles, the magnetically attractable particles can be subjected to a magnetic field gradient such that the magnetically attractable particles can accumulate at an appropriate location in the container. Magnetically attractable particles can be exposed to a magnetic field gradient by movement of the container toward the magnet, by movement of the magnet toward the container, and/or by switching the magnet on and off.

The device may be packaged and distributed to health care facilities and/or at home patients. The devices may be stored in the packaging until ready to use. The packaged components can, optionally, include a magnet to be used in the separation of the magnetically attractable particles from the plasma. Alternatively, the magnet may be packaged separately for use with the single use device.

D. Methods of Processing the Blood Samples

The methods of the invention include processing blood samples to separate the cellular components from the plasma. The method includes contacting the blood samples with the magnetically attractable particles associated with agglutinating agents and applying a magnetic field gradient to the magnetically attractable particles.

The magnetically attractable particles are preferably in a container that can receive the blood sample. The blood samples can then be contacted with the magnetically attractable particles. The magnetically attractable particles can be in the container prior to addition of the blood samples. Alternatively, the magnetically attractable particles can be added after the blood sample has been placed in the container.

Contact of the blood sample with the magnetically attractable particles is generally performed by suspending the magnetically attractable particles in the blood samples. Suspension of the magnetically attractable particles in the blood sample can be performed, for example, by stirring, shaking, vortexing and the like. Preferably, the magnetically attractable particles suspended in the sample bind at least about 90 percent of the red blood cells in the blood sample. More preferably, between about 95 percent and about 100 percent of the red blood cells in the blood sample are bound by the magnetically attractable particles. Even more preferably, between about 99 percent and about 100 percent of the red blood cells in the blood sample are bound by the magnetically attractable particles.

Preferably, the magnetically attractable particles suspended in the sample bind at least about 80 percent of the cellular components in the blood sample. More preferably, between about 90 percent and about 100 percent of the cellular components in the blood sample are bound by the magnetically attractable particles. Even more preferably, between about 99 percent and about 100 percent of the cellular components in the blood sample are bound by the magnetically attractable particles.

The processing time of the blood samples with the magnetically attractable particles can vary. Processing of a blood sample includes contacting the blood sample with the magnetically attractable particles, suspension of the particles in the blood sample, if necessary, and application of a magnetic field gradient to the particles.

The processing time can include time that the particles are suspended in the blood sample for binding the cellular components, i.e. incubation time, and time required to draw the particles to a surface of the container, i.e. separation time. In some embodiments, the particles are incubated in the sample for a period of time prior to application of a magnetic field gradient. In other embodiments, the magnetic field gradient is applied soon after the particles are contacted with the blood sample.

The processing time for the blood samples can generally be between about 30 seconds and about 5 minutes. Preferably, the blood sample is processed with the magnetically attractable particles for between about 30 seconds and about three minutes. More preferably, the blood sample is processed with the magnetically attractable particles for between about 30 seconds and about 2 minutes. It is preferable to have shorter processing times in order to increase the speed of the blood processing. The processing time, however, should be sufficient to bind the cellular components, particularly the red blood cells, in the blood sample. The processing time can be shortened by, for example, increasing the volume of magnetically attractable particles or by using particles having a large surface area onto which cellular components may bind. The processing time can also be shortened by using magnets of greater strength or by using a greater number of magnets.

Preferably, the volume of magnetically attractable particles used for a given blood sample is such that plasma can be obtained in less than about 5 minutes, i.e. processing time, with at least about 90 percent of the red blood cells removed that were in the blood sample. More preferably, the plasma can be obtained in less than about 3 minutes with at least about 95 percent of the red blood cells removed from the blood sample. Even more preferably, the plasma can be obtained in less than about 3 minutes with at least about 99 percent of the red blood cells removed from the blood sample.

After the blood sample has been contacted with the magnetically attractable particles, a magnetic field gradient can be applied to draw the magnetically attractable particles toward the source of the magnetic field gradient. The magnetic field strength in the container is normally stronger at a part of the internal surface of the container closer to the magnet (source of magnetic force) than it is elsewhere. As a result, magnetically attractable particles near the source are subject to greater magnetic force than those farther from it. In one embodiment, two magnets may be located on the opposite sides of the container. Accumulation of the particles at the surfaces close to the source or sources of the magnet field gradient can occur. The plasma as a result is separated from the particles. As described above, the size, shape and the strength of the magnetic field can vary and can be selected based on the blood processing device used and the processing time desired. The processing time can depend, for example, on the number of magnetically attractable particles present in the sample, the size of the particles, the size of the magnet, the number of magnets and the strength of the magnet.

The magnetic field gradient can be applied by placing a selected magnet or magnets near or on the surface of the container with the magnetically attractable particles thereby placing the magnetically attractable particles in a magnetic field gradient. Preferably, the magnet is placed in contact with the outer surface of the container. The magnet may surround the container, be placed in the container and the like. A plurality of magnets may be placed on surfaces around the container. The magnet is preferably placed on a side surface near the bottom of the container.

Application of the magnetic field gradient to the particles can draw the magnetically attractable particles toward the source of the magnetic field gradient. The magnet can be disposed external to the container so as to define a magnetic field gradient. The distance between the magnet and the container may be adjusted so as to create a desired magnetic field strength within the sample in the container. In some embodiments, the device may include means for adjusting the distance between a magnet and the container. The magnetic field strength in the container is normally stronger at a part of the internal surface of the container closer to the magnet (source of magnetic force) than it is elsewhere. As a result, magnetically attractable particles near the source are subject to greater magnetic force than those farther from it. In one embodiment, two magnets may located on the opposite sides of the container.

Generally, at least about 90 percent of the magnetically attractable particles can accumulate at the internal surface of the container. Preferably, between about 95 percent and about 100 percent of the magnetically attractable particles accumulate at internal surface of the container, more preferably at the side of the container.

The plasma can be removed from the container when the magnetically attractable particles have been pulled to an internal surface of the container. The plasma can be removed using a variety of techniques and implements. The plasma can be removed, for example, by pipetting, decanting, siphoning and the like. In a manually operated device, the plasma is preferably removed using a pipet, a dropper or a syringe. In an automated device, the plasma is preferably removed by pipetting, by wicking with an absorbent substrate. In some embodiments, for example in lateral flow devices, plasma may not be removed but may directly travel to other areas of the devices for further analysis. The plasma may travel, for example, from the processing zone to an analytical zone by capillary action. At the analytical zone, other reagents may be present for performing diagnostic assays on the plasma. In some embodiments, substantially all of the plasma may be removed from the container. Alternatively, one or more aliquots may be removed from the container.

The plasma, once removed, can be used for further analysis. Alternatively, the plasma may be stored for future use. The plasma may be stored at refrigeration temperatures, i.e. about 4° C. The plasma may also be frozen, for example, at −20° C. or below.

The processing of the blood sample may also include performing assays for desired analytes using the plasma. The assays can be performed manually by, for example, a technician, a health care worker and/or a patient. The assays may also be performed in an automated device wherein a sample of plasma is removed after separation and used in assays.

The presence or concentration of a number of analytes can be determined using the plasma derived from the methods described herein. Specifically, the plasma can be used in assays to determine the presence and/or concentration of one analyte or a plurality of analytes.

Analytes that can be assayed include toxins, organic compounds, proteins, peptides, microorganisms, amino acids, carbohydrates, nucleic acids, hormones, steroids, vitamins, drugs (including those administered for therapeutic purposes as well as those administered for illicit purposes), virus particles and metabolites of or antibodies to any of the above substances. Analytes that can be assayed include, for example, cholesterol, luteinizing hormone, estradiol, ferritin, creatinine kinase MIB, digoxin, phenytoin, theophylline, vitamin B12, hepatitis B virus surface antigen, alpha fetal protein and drugs of abuse and controlled substances, including amphetamine, methamphetamine, barbituates, cannabinoids and the like.

The specific diagnostic assays that can be used to identify the analytes vary. A number of diagnostic assays for a variety of analytes are known in the field. A procedure for assaying for luteinizing hormone is described, for example, in Abbott $IM_x$ LH assay published by Abbott Laboratories, Chicago, Ill.

The plasma can also be further treated to remove fibrinogen and/or other plasma proteins to obtain serum. Generally, serum can be obtained by allowing the blood sample to clot. Blood samples generally clot spontaneously if anticoagulants, i.e. EDTA, citrate, heparin and the like, are not added to the sample. The serum may then be used to perform diagnostic assays.

EXAMPLES

Example 1

Passive Adsorption of a Lectin onto Paramagnetic Microparticles

This example illustrates the generation of magnetically attractable particles with adsorbed lectin.

Encapsulated paramagnetic microparticles containing about 40 percent by weight of magnetite with a mean diameter of about 1 micron were purchased from Bangs Laboratories, Indianapolis, Ind. A 100 microliter volume of the magnetically attractable particles that were in suspension at about 10 percent solid by weight were measured and used (10 mg. of particles were used). The magnetically attractable particles were centrifuged for about ten minutes at about 10,000 g in a Oster centrifuge Serial No. 10MVS-04755, from Oster, located in Acton, Mass. The supernatant was aspirated to remove the liquid. The pellet was resuspended in a 100 mM bicarbonate buffer, pH 9.5, to a final volume of about 1 percent by weight solids (1000 microliters). The magnetically attractable particles were centrifuged for ten minutes at about 10,000 g and washed with 4000 microliters of the bicarbonate buffer and centrifuged. The supernatant was aspirated. The washing step was repeated one more time and the pellet resuspended to a concentration of about 1 percent solids by weight in the 100 mM bicarbonate buffer (10 mg of particles in 1000 microliters of buffer). The lectin Solanum Tubersum agglutinin (STA) was purchased from Sigma Chemical Co. St. Louis, Mo. The STA was used at a concentration of about 20 micrograms STA for each milligram of particles. The STA was added to the magnetic particle suspension while slowly mixing. The particles were placed on a Clay Adams™ Nutator mixer overnight, Model #421105 purchased from Becton Dickinson, Franklin Lakes, N.J.

The next morning the coated magnetically attractable particles were centrifuged for 10 minutes at about 10,000 g.

The supernatant was aspirated and the pellet was resuspended in a storage buffer or fish skin gelatin (FSG) buffer to 1%, by weight, solids. The storage buffer and the FSG buffer can be used interchangeably. The storage buffer was 100 mM glycine, 2%, by weight, bovine serum albumin, 5%, by weight, sucrose at pH 7.5. The FSG buffer was 2%, by weight, of FSG, 0.2%, by weight, sodium azide, at pH 7.5. The magnetically attractable particles were post-coated in buffer containing bovine serum albumin (BSA) for at least about one hour. Post-coating includes incubating with. BSA so that the BSA can non-specifically bind to the empty sites on the particles. The mixture was sonicated using the Heat Systems Sonicator model #385 for 2 minutes in 2 second burst at a setting of about 20%. The particles were stored at 4° C. until needed.

Example 2

Covalent Coupling of STA to Paramagnetic Microparticles

This example illustrates covalent coupling of a lectin to the magnetically attractable particles.

The magnetically attractable particles and buffers were as described in Example 1. A 100 microliter volume of the magnetically attractable particles that were in suspension at about 10 percent solid by weight were measured and used (10 mg. of particles were used). The magnetically attractable particles were centrifuged for about ten minutes at about 10,000 g in a Oster centrifuge Serial No. 10MVS-04755, from Oster, located in Acton, Mass. The supernatant was aspirated to remove the liquid. The pellet was resuspended in a 100 mM bicarbonate buffer, pH 9.5, to a final volume of about 1 percent by weight solids (1000 microliters). The magnetically attractable particles were centrifuged for ten minutes at about 10,000 g and washed with 4000 microliters of the bicarbonate buffer and centrifuged. The supernatant was aspirated. The washing step was repeated one more time and the pellet resuspended to a concentration of about 1 percent solids by weight in the 100 mM bicarbonate buffer (10 mg of particles in 1000 microliters of buffer). To the particles, 1-[3-(Dimethylamino)propyl]-3-ethyl carbodiimide (EDC) purchased from Sigma Chemical Co., St. Louis, Mo., was added at a concentration of about 20 mM. The required amount of STA was calculated based on a concentration of about 20 micrograms of STA per milligram of magnetically attractable particles. The STA was added to the mixture of the magnetically attractable particles and the EDC while slowly mixing. The magnetically attractable particles were placed in a rotating Nutator mixer for about 2 hours. The magnetically attractable particles were centrifuged for about 10 minutes at 10,000 g. The supernatant was aspirated and the pellet resuspended in FSG buffer or storage buffer to 1%, by weight, solids. The particles were post-coated in the buffer for at least about an hour. The mixture was sonicated for 2 minutes in 2 second bursts with a setting of about 20%. The magnetically attractable particles were stored at 4° C.

Example 3

Passive Adsorption onto Iron Oxide

This examples illustrates the passive adsorption of a lectin to pure iron oxide.

The buffers used were as described in Example 1. About 1 gram of iron oxide #B100M purchased from Delta Colors, Lawrenceville, Ga. was suspended in 10 milliliters (ml) of bicarbonate buffer. The solids concentration in the suspension was about 10%, by weight. The iron oxide particles had a diameter of about 1 micron. The mixture was sonicated for about 0.5 minutes in 2 second bursts with a setting of about 20 percent. The magnetically attractable iron oxide particles were centrifuged for about 10 minutes at 10,000 g. The supernatant was aspirated and the pellet resuspended in bicarbonate buffer to 4 times the volume of 1% by weight solids. The mixture was sonicated again for about 0.5 minute in 2 second bursts at a setting of about 20%. The bicarbonate buffer wash step was repeated 2 more times and the pellet was resuspended in the bicarbonate buffer to about 10% by weight in solids.

The mixture was sonicated for 0.5 minutes in 2 second bursts with a setting of about 20%. About 500 micrograms of STA was added while slowly mixing. The mixing was performed by moving the container back and forth by hand. The reaction mixture was placed on a rotating nutator for at least about 2 hours. The coated magnetically attractable particles were centrifuged for about 10 minutes at 10,000 g. The supernatant was aspirated and the pellet resuspended in storage buffer at about 10% by weight solids. The magnetically attractable particles were centrifuged again and resuspended in storage buffer at about 10% by weight solids. The particles were allowed to postcoat for at least about an hour. The mixture was sonicated for 0.5 minutes in 2 second bursts with a setting of about 20%. The coated magnetically attractable particles were stored at 4° C. until needed.

Example 4

The Effect of Magnetic Field Gradient on Separation of Blood Components

This example illustrates the effect of varying magnetic field gradients on separation of the magnetically attractable particles from the liquid fraction.

The magnetically attractable particles that were used are as described in Example 1. These magnetically attractable particles were coated with passively adsorbed STA as in Example 1. The particles had a mean diameter of about 1 micron. Magnets were purchased from Dexter Magnetic Technology Inc. Fremont, Calif. Magnets that were used had strength of about 14,000 gauss, 12,000 gauss or about 10,000 gauss. The blood sample size was about 100 microliters. A 100 microliter volume of the magnetically attractable particles prepared in Example 1 were used. After separation, the plasma volume was determined by the use of a microsyringe. Classical particles refers to non-encapsulated particles.

Table 1 shows the results obtained when the magnet strength is varied, the sample size is varied and/or the amount and type of magnetically attractable particles is varied. The processing time is the time from addition of the sample with the magnetically attractable particles until the separation of the plasma from the particles.

TABLE 1

| Magnetite % of Particle | Magnet Strength (Gauss) | Plasma Vol. (uL)/Proc. Time (min) |
|---|---|---|
| 20% encapsulated | 14,000 | 40 uL/3 min. |
| 40% encapsulated | 14,000 | 45 uL/2 min. |
| 60% Classical | 14,000 | /5 min. |
| 40% encapsulated | 10,000 | 35 uL/4 min. |

TABLE 1-continued

| Magnetite % of Particle | Magnet Strength (Gauss) | Plasma Vol. (uL)/Proc. Time (min) |
|---|---|---|
| 40% encapsulated | 12,000 | 35 uL/3.5 min. |
| 40% encapsulated | 2small rectangular ma. | 35 uL/3 min. |

The results in table 1 indicate that use of more direct and stronger magnetic field gradients results in faster separation times and higher yield of plasma. In addition, two smaller magnets can provide processing times and plasma volumes comparable to a 14,000 gauss magnet.

Example 5

Yield of Plasma from Whole Blood

This example illustrates the amount of plasma that was generated from whole blood using magnetically attractable particles.

STA passively coated magnetically attractable particles as described in example 1 were used. The magnetically attractable particles had a mean diameter of about 1 micron and contained about 40% magnetite. The two small rectangular magnets described in Example 4 of about 14,000 gauss were used. A whole blood sample #F20130 having a hematocrit of about 40% was used. The hematocrit was tested on a Spin-pro hematocrit tester purchased from Bio/Data Corporation, Horsham, Pa.

TABLE 2

| Vol. of 1% solids MP | 50 uL | 100 uL | 100 uL | 300 uL | 1000 uL |
|---|---|---|---|---|---|
| Vol. of Whole Blood | 50 uL | 1000 uL | 250 uL | 1000 uL | 4000 uL |
| Plasma yield | 20 uL | 45 uL | 80 uL | 300 uL | 1700 uL |
| Time to process | 1.5 min. | 1.5 min. | 2.5 min. | 5 min. | 5 min. |

Table 2 shows results from a number of samples with varying volumes of magnetically attractable particles and volume of whole blood. The plasma yield and the processing time were determined for each sample. The amount of plasma obtained increased as the amount of whole blood was increased. Small samples of blood can be processed in relatively short times of about 1.5 minutes. Increasing sample sizes required longer processing times, however, these were still highly desirable separation times. A blood sample of about 4 mls required only 5 minutes.

Example 6

Preparation of Dry Magnetically Attractable Particles

This example illustrates various methods for preparation of dry magnetically attractable particles.

Magnetically attractable particles were prepared as in Example 1. The particles had a mean diameter of about 1 micron and were about 40 percent by weight magnetite.

The magnetically attractable particles were dried down by lyophilization. In lyophilization, cups were placed in trays. A sample of 100 microliters of the magnetically attractable particles were hand spotted into the cup. The temperature was set at about 20° C. and the sample was lyopholized overnight in a lyophilizer Model #651M-24F40 purchased from Hull Company, Halboro, Pa. After lyophilization, the cups were sealed on micro-tool sealing line and stored at about 4° C. in a plastic bag with desiccant. The cup sealing machine was built by Advent Design Bristol, Pa.

The magnetically attractable particles were also dried down in an oven. A sample of 100 microliters of the magnetic particle was hand spotted into a cup and the cup placed in trays. The sample was dried at about 50° C. for about 2 hours in a drying oven Model Micro-20 WS from Micro Tool Co. Ashby, Mass. After drying, the cups were sealed on micro-tool sealing line and stored at about 4° C. in a plastic bag with desiccant.

The magnetically attractable particles were also dried down in a vacuum oven model#583, from National Appliance Co. A sample of 100 microliters of the magnetically attractable particles was hand spotted into a cup. The cups were placed in a small finger type test tube rack. The samples were dried in a desiccated vacuum oven at about 40° C. at about 1 atm for about 2 hours. The cups were sealed on micro-tool sealing line and stored in a plastic bag with desiccant.

The magnetically attractable particles were also formed into tablets. Magnetic micro-particles were converted into tablets by a commercial method, for example, Biolyph, Minnetonka, Minn. Tablets were stored in evacuated, sealed 10 mL glass vials at 4° C.

TABLE 3

|  | Lyophilized | Oven-Dried | Vacuum Oven | Tablets |
|---|---|---|---|---|
| Particles Vol. (uL) | 100 | 100 | 100 | 120 |
| Whole Blood (uL) | 250 | 250 | 250 | 250 |
| Time for Resuspension | 5 sec | 30 sec | 30 sec | 10 sec |
| Time for processing | 3 min | 3.5 min | 3.5 min | 3 min |
| Vol. Of Plasma (uL) | 75 | 75 | 75 | 75 |

Results from the use of the dried down magnetically attractable particles prepared using the methods described above are shown in Table 3. The lyophilized and the tablet form resuspended quickly, determined by visual observation, relative to the other dried preparations. Processing times were slightly better for lyophilized and tablet forms. All of them resulted in the same volume of plasma. A slightly higher amount of magnetically attractable particles were necessary to obtain the tablet form. Dried down particles prepared in any of the described methods resulted in functional magnetically attractable particles.

Example 7

Blood Cellular Content After Magnetic Separation

This example illustrates the percentage of cellular material remaining in the plasma after treatment with magnetically attractable particles.

The magnetically attractable particles described in Example 1 were used. In three separate tubes, whole blood samples were separated using the magnetically attractable particles. Each of the tubes also contained one of the three anti-coagulants-ethylenediamine tetraacetate (EDTA), heparin or citrate. The plasma derived from the blood sample after magnetic separation was analyzed for cellular composition on a Beckman Coulter, Flow cytometer, Epic Elite, Fullerton, Calif. Thiazole orange (TO) was used to differentiate the erythrocytes from the leukocytes.

The results from the cellular analysis of each of three tubes is shown in Table 4. The amount of the indicated cellular components was determined. Values are based on particles counted (PLT, RBC and LEU) using Beckman Coulter Flow Cytometer before and after. The red blood cells in all of the sample were removed efficiently. Citrate yielded the best results in removing platelets, erythrocytes and leukocytes.

TABLE 4

| Anti-coag. | PLT | RBC | LEU |
|---|---|---|---|
| EDTA | 63.499% | 0.004% | 10.741% |
| Heparin | 5.188% | 0.004% | 7.639% |
| Citrate | 2.254% | 0.002% | 7.379% |

Example 8

Estradiol and LH Immunoassays of Magnetically Separated Plasma

This example compares the methods of detecting analytes using centrifugation with the methods of detecting analytes using magnetically attractable particles.

Whole blood samples were collected and spiked with differing levels of luteinizing hormone (LH) or estradiol (E2). The blood samples were then divided into two parts. One part was centrifuged at about 2000 g for about 15 minutes. The second part was separated using the STA coated magnetically attractable particles described in example 1. The plasma was collected from both of the methods and analyzed for the analyte, either E2 or LH, using an Abbott $IM_x$ system purchased from Abbott Laboratories, Chicago, Ill. The Abbott $IM_x$ assay was performed according to the instructions in the Abbott $IM_x$ assay kit, incorporated herein by reference. Briefly, the assay is a microparticle enzyme immunoassay. Microparticles are coated with an anti-LH antibody. The LH binds to the antibody coated particles forming an antibody-antigen complex. The complex bound to the microparticles is transferred to a glass fiber matrix to which the microparticles bind irreversibly. The matrix is washed to remove unbound materials and an anti LH specific alkaline phosphatase conjugate is added that binds to the antigen-antibody complex. The matrix is washed and substrate, 4-Methylumoelliferyl Phosphate is added to the matrix and the fluorescent product is measured by the fluorometer.

Blood samples were spiked with LH. Plasma was derived from these samples using both the centrifugation method and also the magnetically attractable particles. The LH was analyzed using the Abbott IMX assay described above.

Figure 2:
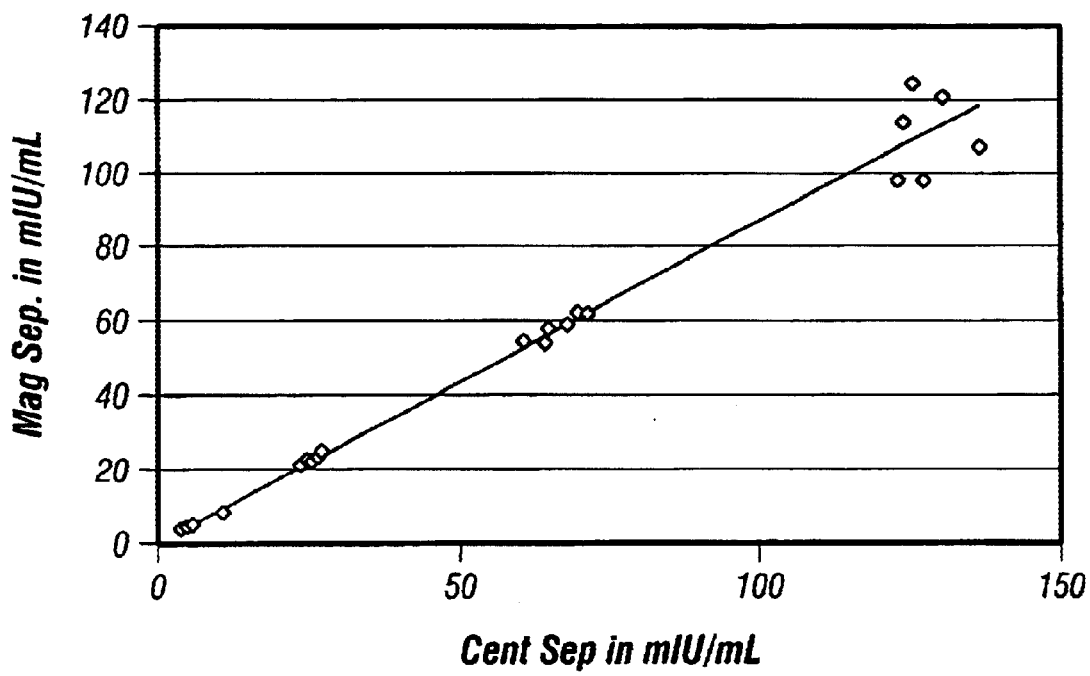
FIG. 2 is a plot comparing luteinizing hormone levels obtained from plasma separated from magnetically attractable particles and plasma derived from centrifugation.
Figure 3:
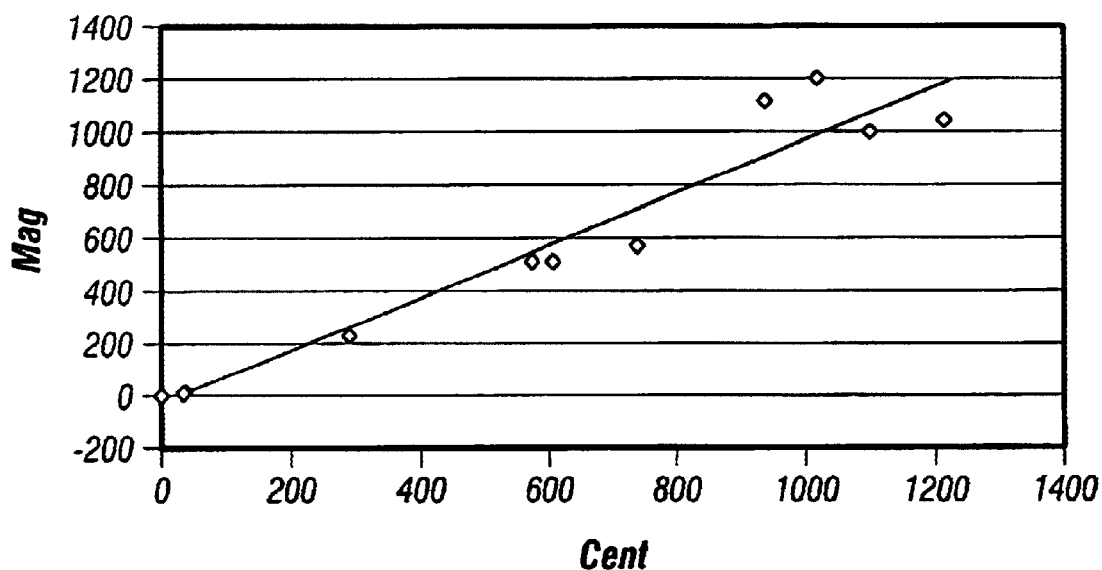
FIG. 3 is a plot comparing estradiol levels obtained from plasma separated from magnetically attractable particles and plasma derived from centrifugation.
Figure 4:
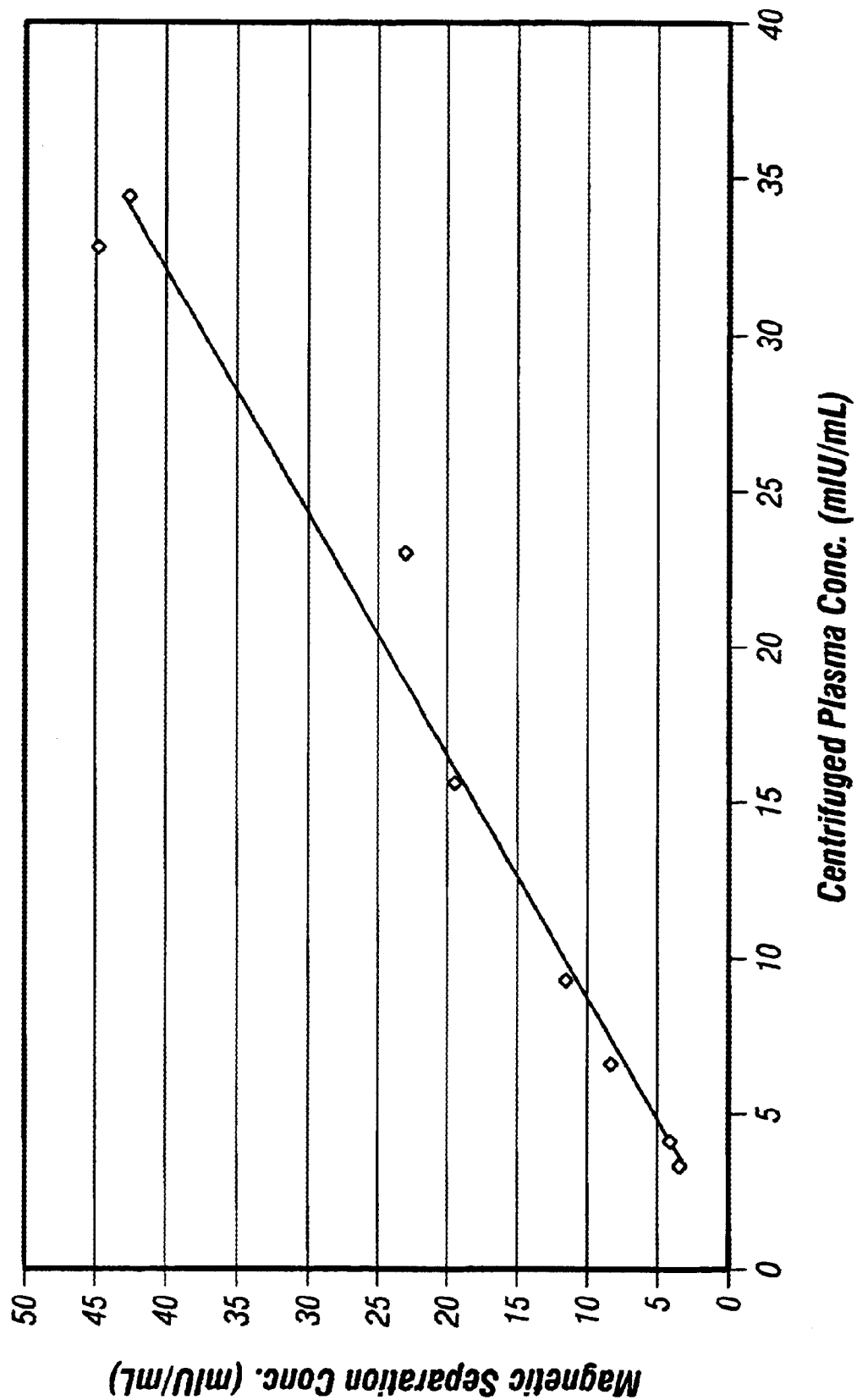
FIG. 4 is a plot comparing luteinizing hormone levels obtained from plasma separated from magnetically attractable particles and plasma derived from centrifugation. The assays were performed using a Copalis II system.

The results from analysis of LH content are shown in Table 5 and illustrated in FIG. 2. The results from analysis of E2 content are shown in Table 6 and illustrated in FIG. 3. The left hand columns show values obtained when the plasma was obtained by centrifugation. The right hand columns show values obtained when the plasma was obtained by processing using magnetically attractable particles. The results indicate that plasma derived from centrifugation or processing with the magnetically attractable particles can be used to analyze the LH content and E2 content in the plasma. Plasma derived from either method yielded similar concentrations of the analyte.

TABLE 5

| Lh Conc. in plasma mlu/mL | Lh Conc. Mag.Sep. Plasma mlu/ml |
|---|---|
| 4.31 | 4.16 |
| 25.46 | 22.78 |
| 70.76 | 61.76 |
| 122.8 | 113.1 |
| 24.23 | 22.71 |
| 67.25 | 59.24 |
| 135.35 | 106.38 |
| 3.47 | 2.8 |
| 24.93 | 21.42 |
| 68.5 | 62.46 |
| 129.19 | 120.6 |
| 4.53 | 4.22 |
| 23.07 | 21.19 |
| 63.2 | 53.84 |
| 121.99 | 98.01 |
| 5.25 | 4.89 |
| 27 | 25.4 |
| 63.64 | 57.53 |
| 124.3 | 123.41 |
| 10.2 | 8.84 |
| 26.78 | 24.23 |
| 59.88 | 54.01 |
| 126.4 | 98.5 |

TABLE 6

| E2 Conc. in Plasma pg/ml | E2 Conc. Mag.Sep. Plasma pg/ml |
|---|---|
| 30.97 | 30.7 |
| 928.13 | 1126.99 |
| 37.54 | 32.13 |
| 1093.55 | 1002.8 |
| 38.88 | 35.81 |
| 1010.68 | 1198.55 |
| 30.38 | 27.38 |
| 560.7 | 511.58 |
| 1214.33 | 1044.71 |
| 33.93 | 11.03 |
| 277.77 | 229.95 |
| 588.42 | 523.32 |
| 5.08 | 9.59 |
| 724.53 | 567.4 |

Example 9

Copalis II LH Assay Using On-line Magnetic Particle Separated Plasma

This example illustrates a separation and analysis using an automated system.

A blood sample of about 400 microliters was pipetted into the sample well of the Copalis II disposable cup. The cup was loaded into the instrument. The Copalis II conducted a fully automated procedure. The instrument transferred 250 microliters of the blood sample into the separation well that contains the dried magnetic particle reagent dried down in a drying oven. The instrument mixes the blood sample with the magnetically attractable particles by repeat pipetting 3 times to suspend the magnetically attractable particles with the blood sample. Separation of blood cells from plasma occurred by the magnetic field generated by two small rectangular magnets, as described in Example 4, that were in close proximity to the separation well. A measured volume of the separated plasma aspirated by the Copalis II dispensing probe was transferred to the reaction well. The reaction well contained 1.8 micron polystyrene microparticle coated with a monoclonal antibody, anti-LH antibody, in 180 microliters of reaction buffer. The reaction well also contained an Inert Reference Particle (IRP). The purpose of the IRP was to control the counting time when the beads were later on passed through the flow cell. Colloidal gold particles, about 100 nanomolar, coated with another anti-LH monoclonal antibody were transferred into the reaction well. The reaction well was incubated for about 25 minutes. A sample of the reaction mixture was injected into the flow cell. The instrument was programmed to count 2500 IRP beads then stop. Laser Forward Light Scatter and Side Scatter of the reaction bead was measured. Mathematical algorithms together with pre-established standard curves were used for the quantitation of LH concentration in the blood sample. LH concentration can be received as a direct printout of test results, or on-line transferred through Laboratory Information Management Systems. The results of the test are shown in FIG. 5. LH test results were generated in less than 30 minutes from blood draw.

Although the present invention has been described with reference to preferred embodiments, workers skilled in the art will recognize that changes may be made in form and detail without departing from the spirit and scope of the invention.

What is claimed is:

1. A method for processing blood comprising:
   providing blood comprising cellular components and plasma, said plasma comprising positively and negatively charged analytes;
   providing a magnetically attractable particle associated with an agglutinating agent, said agglutinating agent capable of selectively binding to said cellular components and not to said analytes;
   contacting said blood with said magnetically attractable particle associated with said agglutinating agent to form a complex; and
   subjecting said contacted blood to a magnetic field to separate said complex from said plasma.

2. The method according to claim 1, wherein said blood is whole blood.

3. The method according to claim 1, wherein said magnetically attractable particle is treated with an agent selected from the group consisting of latex, cellulose, polyacrolein, polyacrylamide, and silane, said treatment occurring prior to said association of said magnetically attractable particle with said agglutinating agent.

4. The method according to claim 1, wherein said analytes present in plasma are selected from the group consisting of toxins, organic compounds, proteins, peptides, microorganisms, amino acids, carbohydrates, nucleic acids, hormones, steroids, vitamins, drugs, virus particles, and combinations thereof.

5. The method according to claim 4, wherein said analytes present in plasma are selected from the group consisting of cholesterol, luteinizing hormone, estradiol, ferritin, creatinine kinase MIB, digoxin, phenytoin, theophylline, vitamin B12, hepatitis B virus surface antigen, alpha fetal protein, amphetamines, methamphetamine, barbiturates, and cannabinoids.

6. The method according to claim 1, wherein said contacting step and said subjecting step occur simultaneously.

7. The method of claim 1 wherein said agglutinating agent comprises a lectin.

8. The method of claim 7 wherein said lectin is Solanum Tubersum agglutinin.

9. The method of claim 1 wherein said cellular components comprise erythrocytes, leukocytes, platelets and combinations thereof.

10. The method of claim 1 wherein said agglutinating agent is adsorbed onto said magnetically attractable particle.

11. The method of claim 1 wherein said agglutinating agent is covalently coupled to said magnetically attractable particle.

12. The method of claim 1 wherein the diameter of said magnetically attractable particles is between about 0.1 microns and about 100 microns.

13. The method of claim 1 wherein the mean diameter of said magnetically attractable particle is about 1 micron.

14. The method of claim 1 wherein the volume of blood being processed is about 100 microliters or less.

15. The method of claim 1 wherein said magnetically attractable particles is in about a 1 percent by weight suspension, wherein between about 25 microliters and about 100 microliters of said suspension can bind at least about 90 percent by weight of the red blood cells in a 100 microliter blood sample.

16. The method of claim 1 wherein said magnetic field is created by a neodymium magnet of 14,000 gauss.

17. The method of claim 1 wherein said agglutinating agent binds greater than about 90 percent by weight of the red blood cells in said blood.

18. The method of claim 1 further comprising contacting said blood with an anti-coagulant.

19. The method of claim 1 further comprising contacting said blood with a non-hemolytic surfactant.

20. The method of claim 18 wherein said magnetically attractable particle has a concentration of between about 0.2 micrograms agglutinating agent per milligram of magnetically attractable particle and about 10 micrograms of agglutinating agent per milligram of magnetically attractable particle.

21. The method of claim 5 further comprising assaying said separated plasma for the presence or absence of one or more of said analytes.

22. The method of claim 21 wherein said agglutinating agent does not bind to said analytes present in said plasma.

23. The method of claim 1 wherein said contacting and said subjecting steps are performed in less than about five minutes.

24. The method of claim 21 wherein said contacting and said subjecting steps are performed in less than about three minutes.

25. The method of claim 21 wherein said blood processing is adapted to be used in connection with a fully automated system.

26. The method of claim 21 wherein said separated plasma assaying is adapted to be performed with a lateral flow device.

27. A method for processing blood comprising:
   providing blood comprising cellular components and plasma;
   providing a magnetically attractable particle associated with an agglutinating agent, said agglutinating agent capable of selectively binding to said cellular components;
   contacting said blood with said magnetically attractable particle to form a complex; and
   subjecting said contacted blood to a magnetic field to separate said complex from said plasma to result in magnetically-separated plasma, wherein said magnetically-separated plasma is substantially equivalent to centrifugation-derived plasma.

28. The method according to claim 1 or claim 27, wherein a unit or more of said blood is drawn from a vein.

29. A device for processing blood, said blood comprising cellular components and plasma, said plasma comprising positively and negatively charged analytes, to separate said cellular components from said plasma, said device comprising a container having magnetically attractable particles associated with an agglutinating agent, said agglutinating agent capable of selectively binding to said cellular components and not to said positively and negatively charged analytes, wherein the volume of said magnetically attractable particles in said container is selected such that when a magnetic field is applied to a suspension of said magnetically attractable particles, said magnetically attractable particles accumulate in less than about 5 minutes at a surface of said container near to said magnetic field, and wherein at least about 0.2 micrograms of said agglutinating agent is associated with about 1 milligram of said magnetically attractable particles.

30. A device for processing blood, said blood comprising cellular components and plasma, said plasma comprising positively and negatively charged analytes, to separate said cellular components from said plasma, said device comprising a container having magnetically attractable particles associated with an agglutinating agent, said agglutinating agent capable of selectively binding to said cellular components and not to said positively and negatively charged analytes, wherein the volume of said magnetically attractable particles in said container is selected such that when a magnetic field is applied to a suspension of said magnetically attractable particles, said magnetically attractable particles accumulate in less than about 5 minutes at a surface of said container near to said magnetic field, and wherein between about 1 microgram and about 5 micrograms of said agglutinating agent is associated with about 1 milligram of said magnetically attractable particles.

31. A device for processing blood, said blood comprising cellular components and plasma, said plasma comprising positively and negatively charged analytes, to separate said cellular components from said plasma, said device comprising a container having magnetically attractable particles associated with an agglutinating agent, said agglutinating agent capable of selectively binding to said cellular components and not to said positively and negatively charged analytes, wherein the volume of said magnetically attractable particles in said container is selected such that when a magnetic field is applied to a suspension of said magnetically attractable particles, said magnetically attractable particles accumulate in less than about 5 minutes at a surface of said container near to said magnetic field, and wherein said magnetically attractable particles are in a suspension.

32. A device for processing blood, said blood comprising cellular components and plasma, said plasma comprising positively and negatively charged analytes, to separate said cellular components from said plasma, said device comprising a container having magnetically attractable particles associated with an agglutinating agent, said agglutinating agent capable of selectively binding to said cellular components and not to said positively and negatively charged analytes, wherein the volume of said magnetically attractable particles in said container is selected such that when a magnetic field is applied to a suspension of said magnetically attractable particles, said magnetically attractable particles accumulate in less than about 5 minutes at a surface of said container near to said magnetic field, and wherein said magnetically attractable particles are in a dry form.

33. The device of claim 32 wherein said magnetically attractable particles are lyophilized magnetically attractable particles.

34. The device of claim 32 wherein said magnetically attractable particles are oven dried magnetically attractable particles.

35. The device of claim 32 wherein said magnetically attractable particles are in a tablet form.

36. A device for processing blood, said blood comprising cellular components and plasma, said plasma comprising positively and negatively charged analytes, to separate said cellular components from said plasma, said device comprising a container having magnetically attractable particles associated with an agglutinating agent, said agglutinating agent capable of selectively binding to said cellular components and not to said positively and negatively charged analytes, wherein the volume of said magnetically attractable particles in said container is selected such that when a magnetic field is applied to a suspension of said magnetically attractable particles, said magnetically attractable particles accumulate in less than about 5 minutes at a surface of said container near to said magnetic field, and wherein said magnetically attractable particles accumulate in less than about 3 minutes.

37. A device for processing blood, said blood comprising cellular components and plasma, said plasma comprising positively and negatively charged analytes, to separate said cellular components from said plasma, said device comprising a container having magnetically attractable particles associated with an agglutinating agent, said agglutinating agent capable of selectively binding to said cellular components and not to said positively and negatively charged analytes, wherein the volume of said magnetically attractable particles in said container is selected such that when a magnetic field is applied to a suspension of said magnetically attractable particles, said magnetically attractable particles accumulate in less than about 5 minutes at a surface of said container near to said magnetic field, and wherein said container further comprises an anti-coagulant.

38. The device of claim 37 wherein said anti-coagulant is selected from the group consisting of EDTA, heparin, and citrate.

39. A device for processing blood, said blood comprising cellular components and plasma, said plasma comprising positively and negatively charged analytes, to separate said cellular components from said plasma, said device comprising a container having magnetically attractable particles associated with an agglutinating agent, said agglutinating agent capable of selectively binding to said cellular components and not to said positively and negatively charged analytes, wherein the volume of said magnetically attractable particles in said container is selected such that when a magnetic field is applied to a suspension of said magnetically attractable particles, said magnetically attractable particles accumulate in less than about 5 minutes at a surface of said container near to said magnetic field, and wherein said container further comprises a non-hemolytic surfactant.

40. A device for processing blood, said blood comprising cellular components and plasma, said plasma comprising positively and negatively charged analytes, to separate said cellular components from said plasma, said device comprising a container having magnetically attractable particles associated with an agglutinating agent, said agglutinating agent capable of selectively binding to said cellular components and not to said positively and negatively charged analytes, wherein the volume of said magnetically attractable particles in said container is selected such that when a magnetic field is applied to a suspension of said magnetically attractable particles, said magnetically attractable particles accumulate in less than about 5 minutes at a surface of said container near to said magnetic field, and wherein said volume of said magnetically attractable particles in said container is sufficient to bind at least about 95 percent of red blood cells in blood.

41. A device for processing blood, said blood comprising cellular components and plasma, said plasma comprising positively and negatively charged analytes, to separate said cellular components from said plasma, said device comprising a container having magnetically attractable particles associated with an agglutinating agent, said agglutinating agent capable of selectively binding to said cellular components and not to said positively and negatively charged analytes, wherein the volume of said magnetically attractable particles in said container is selected such that when a magnetic field is applied to a suspension of said magnetically attractable particles, said magnetically attractable particles accumulate in less than about 5 minutes at a surface of said container near to said magnetic field, and wherein said volume of said magnetically attractable particles in said container is sufficient to bind at least about 99 percent of red blood cells in blood.

42. A device for processing blood, said blood comprising cellular components and plasma, said plasma comprising positively and negatively charged analytes, to separate said cellular components from said plasma, said device comprising a container having magnetically attractable particles associated with an agglutinating agent, said agglutinating agent capable of selectively binding to said cellular components and not to said positively and negatively charged analytes, wherein the volume of said magnetically attractable particles in said container is selected such that when a magnetic field is applied to a suspension of said magnetically attractable particles, said magnetically attractable particles accumulate in less than about 5 minutes at a surface of said container near to said magnetic field, and further comprising a magnet.

43. The device of claim 42 wherein said magnet is between about 1000 gauss and about 20,000 gauss.

44. A device for processing blood, said blood comprising cellular components and plasma, said plasma comprising positively and negatively charged analytes, to separate said cellular components from said plasma, said device comprising a container having magnetically attractable particles associated with an agglutinating agent, said agglutinating agent capable of selectively binding to said cellular components and not to said positively and negatively charged analytes, wherein the volume of said magnetically attractable particles in said container is selected such that when a magnetic field is applied to a suspension of said magnetically attractable particles, said magnetically attractable particles accumulate in less than about 5 minutes at a surface of said container near to said magnetic field, and further comprising one or more components for analyzing the presence or absence of an analyte in said plasma.

45. The device of claim 44 wherein said components are selected from the group consisting of pipets, analytical components, reagents for assays, binding partners, indicators and combinations thereof.

46. A reagent to separate cellular components from plasma, said cellular components and said plasma present in blood, said reagent comprising magnetically attractable particles associated with an agglutinating agent, said agglutinating agent capable of selectively binding to said cellular components and not to positively and negatively charged analytes present in said plasma, wherein the volume of said magnetically attractable particles is such that when said magnetically attractable particles are in suspension, said magnetically attractable particles are drawn away from the liquid of said blood in less than about five minutes when a magnetic field is applied, and wherein at least about 0.2 micrograms of said agglutinating agent is associated with about 1 milligram of said magnetically attractable particles.

47. A reagent to separate cellular components from plasma, said cellular components and said plasma present in blood, said reagent comprising magnetically attractable particles associated with an agglutinating agent, said agglutinating agent capable of selectively binding to said cellular components and not to positively and negatively charged analytes present in said plasma, wherein the volume of said magnetically attractable particles is such that when said magnetically attractable particles are in suspension, said magnetically attractable particles are drawn away from the liquid of said blood in less than about five minutes when a magnetic field is applied, and wherein between about 1 microgram and about 5 micrograms of said agglutinating agent is associated with about 1 milligram of said magnetically attractable particles.

48. A reagent to separate cellular components from plasma, said cellular components and said plasma present in blood, said reagent comprising magnetically attractable particles associated with an agglutinating agent, said agglutinating agent capable of selectively binding to said cellular components and not to positively and negatively charged analytes present in said plasma, wherein the volume of said magnetically attractable particles is such that when said magnetically attractable particles are in suspension, said magnetically attractable particles are drawn away from the liquid of said blood in less than about five minutes when a magnetic field is applied, and wherein said magnetically attractable particles are in suspension.

49. A reagent to separate cellular components from plasma, said cellular components and said plasma present in blood, said reagent comprising magnetically attractable particles associated with an agglutinating agent, said agglutinating agent capable of selectively binding to said cellular components and not to positively and negatively charged analytes present in said plasma, wherein the volume of said magnetically attractable particles is such that when said magnetically attractable particles are in suspension, said magnetically attractable particles are drawn away from the liquid of said blood in less than about five minutes when a magnetic field is applied, and wherein said magnetically attractable particles are in a dry form.

50. The reagent of claim 49 wherein said magnetically attractable particles are lyophilized magnetically attractable particles.

51. The reagent of claim 49 wherein said magnetically attractable particles are oven dried magnetically attractable particles.

52. The reagent of claim 49 wherein said magnetically attractable particles are vacuum oven dried magnetically attractable particles.

53. The reagent of claim 49 wherein said magnetically attractable particles are in a tablet form.

* * * * *